(12) United States Patent
Conklin

(10) Patent No.: US 11,872,129 B2
(45) Date of Patent: Jan. 16, 2024

(54) SYSTEM AND METHOD FOR HOLDING AND DELIVERING A SURGICAL HEART VALVE

(71) Applicant: JVH of America, Irvine, CA (US)

(72) Inventor: Brian Scott Conklin, Orange, CA (US)

(73) Assignee: Jilin Venus Haoyue Medtech Limited, Changchun (CN)

( * ) Notice: Subject to any disclaimer, the term of this patent is extended or adjusted under 35 U.S.C. 154(b) by 205 days.

(21) Appl. No.: 17/496,082

(22) Filed: Oct. 7, 2021

(65) Prior Publication Data

US 2023/0111820 A1    Apr. 13, 2023

(51) Int. Cl.
*A61F 2/24* (2006.01)

(52) U.S. Cl.
CPC .... *A61F 2/2427* (2013.01); *A61F 2220/0075* (2013.01); *A61F 2220/0083* (2013.01)

(58) Field of Classification Search
CPC .................................................... A61F 2/2427
See application file for complete search history.

(56) References Cited

U.S. PATENT DOCUMENTS

| | | | |
|---|---|---|---|
| 5,776,187 A | 7/1998 | Krueger et al. | |
| 8,202,314 B2 | 6/2012 | Stobie | |
| 8,641,757 B2 | 2/2014 | Pintor et al. | |
| 9,101,471 B2 | 8/2015 | Kleinschrodt | |
| 9,788,931 B2 | 10/2017 | Giordano et al. | |
| 9,848,984 B2 | 12/2017 | Conklin et al. | |
| 10,463,485 B2 | 11/2019 | Conklin et al. | |
| 10,588,743 B2 | 3/2020 | Campbell et al. | |
| 10,799,353 B2 | 10/2020 | Bordoloi Gurunath et al. | |
| 2004/0138741 A1 | 7/2004 | Stobie et al. | |
| 2005/0251252 A1 | 11/2005 | Stobie | |
| 2006/0015177 A1 | 1/2006 | Quest et al. | |
| 2008/0071367 A1 | 3/2008 | Bergin et al. | |
| 2009/0076599 A1 | 3/2009 | Bergin | |
| 2009/0198323 A1 | 8/2009 | Johnson et al. | |
| 2009/0259305 A1* | 10/2009 | Lane ..................... | A61F 2/2427 623/2.11 |
| 2011/0093064 A1 | 4/2011 | Bergin | |
| 2014/0316519 A1* | 10/2014 | Veseley ................. | A61F 2/2427 623/2.11 |
| 2018/0289477 A1* | 10/2018 | Conklin ............... | A61F 2/2439 |
| 2019/0224009 A1 | 7/2019 | Conklin | |
| 2020/0113682 A1 | 4/2020 | Chang et al. | |

(Continued)

FOREIGN PATENT DOCUMENTS

| | | |
|---|---|---|
| EP | 0859575 A1 | 8/1998 |
| EP | 1009331 A1 | 6/2000 |
| EP | 3563799 A1 | 11/2019 |

(Continued)

*Primary Examiner* — Suba Ganesan
(74) *Attorney, Agent, or Firm* — Raymond Sun

(57) ABSTRACT

The present invention provides a system and method for retaining, positioning and releasing a prosthetic heart valve. The system includes a valve holder, and a control handle. The valve holder includes a connection base and at least one holding arm. The holding arms are distributed around a periphery of the connection base, with the holding arms having positioning structures at the distal side thereof for engaging with an outflow side of the prosthetic heart valve. The control handle is coupled to the valve holder for controlling the valve holder.

20 Claims, 14 Drawing Sheets

(56) References Cited

U.S. PATENT DOCUMENTS

2021/0052381 A1 2/2021 Bergin et al.

FOREIGN PATENT DOCUMENTS

| EP | 3795119 A1 | 3/2021 |
| EP | 3799836 A1 | 4/2021 |
| WO | WO2003/034950 A1 | 5/2003 |
| WO | WO2020/163145 A1 | 8/2020 |

* cited by examiner

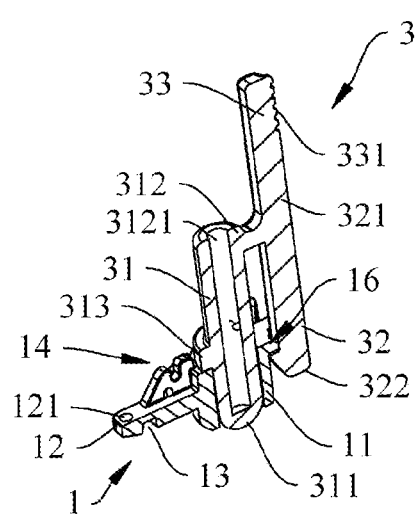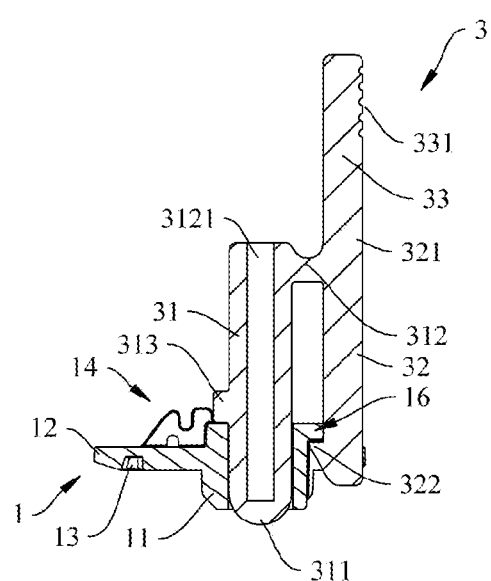
FIG. 8c
FIG. 8d

SYSTEM AND METHOD FOR HOLDING AND DELIVERING A SURGICAL HEART VALVE

TECHNICAL FIELD

The present invention relates to the field of medical devices, and in particular, to a system and a method for holding, delivering and releasing a prosthetic heart valve to a valve annulus of a patient, the system including valve holders, control handles and prosthetic heart valves.

BACKGROUND

Aortic valve disease, especially aortic stenosis, has a high mortality rate and brings a huge burden on health care systems around the world. Prosthetic valve replacement is the most common treatment for the diseased aortic valve. There are two types of methods for biological aortic valve replacement: surgical replacement and transcatheter interventional replacement. Due to lack of long-term durability data for transcatheter valves, young patients (e.g., under 65 years of age) and patients with low surgical risk are often treated by receiving a surgically-replaced heart valve.

Surgical prosthetic heart valves are typically attached to a holder which is sewn or otherwise attached to the heart valve. During a surgical aortic valve replacement procedure, the valve holder is attached to a handle that extends in the outflow direction of the valve by 20 or more cm. The handle and holder combination allows the valve to be held stably by an assistant while the surgeon places the annular sutures in the sewing cuff of the prosthesis. By holding the handle instead of the valve, contact with the valve is minimized thereby reducing the chances for contamination.

Once the annular sutures are placed in the sewing cuff, the valve is "parachuted" down the sutures by holding slight tension on the sutures while pushing the valve toward the annulus with the handle. Once the valve is seated on the annulus, the holder and handle are usually detached and removed from the valve to remove them from the line-of sight and allow easier access to the valve for tying the sutures.

The present inventors have found that surgical valve replacement has some problems. The main problem is that once the surgical valve is positioned at the native annulus, the valve holder may interfere with securing of the valve to the annulus by obstructing the surgeon's access to the valve sewing ring for knot tying of the annular sutures. In some cases, the valve holder is mounted on or near the sewing ring, which will interfere with the operations on the sewing ring during the surgical procedure. In some other cases, the holder attaches to the commissure tips and protrudes outward slightly from them, thereby making access to the sewing ring adjacent to the commissures difficult, especially in patients with a tight aorta.

Another common challenge with current holder designs is that sutures must be cut at three locations on the holders to remove them from the heart valve. The three cut-points may not all be easy to access for anatomical reasons. Having multiple cut-points could add to procedure time and add increased risk to the patient due to the need to use a sharp cutting instrument in the aorta at multiple locations.

The handles on most current halve holders are usually attached to the holders with a threaded interface. This creates a few challenges. During most aortic valve replacement procedures, the handle used to hold the heart valve is bent by the surgeon such that the heart valve will be aligned coaxially with the aortic annulus. Owing to this bend, however, the handle cannot be simply unscrewed from the valve holder once the heart valve is parachuted to the annulus. Once the heart valve is at the annulus, the handle will get in the way of tying knots at the sewing cuff. As such, surgeons generally remove the handle and holder together at that point in the procedure by cutting the holder from the heart valve. This leaves the heart valve exposed and unprotected during the remainder of the procedure.

Another shortcoming of many current holder designs is they have a relatively high profile above the heart valve. This added height can create challenges when navigating through tight anatomy. This can lead to difficulty in implanting the heart valve and potential procedural delays.

Given the above challenges with existing valve holder designs, there is a need for a handle and holder system that would incorporate the following features:
Easy access to all areas of the sewing cuff;
Ease of removing the handle from the holder;
Ease of removing the holder from the valve; and
Low profile to facilitate ease of implantation.

SUMMARY

The present invention provides a holder and handle system for a surgical aortic valve bioprosthesis that incorporates improved access to the sewing cuff for ease of implantation, a single cut-point for removing the holder from the heart valve, a quick release mechanism to release the holder from the handle, and an extremely low profile to further ease implantation.

In one aspect, the present invention provides a valve holder for delivering a prosthetic heart valve, which includes a connection base and at least one holding arm. The connection base has an axial direction, wherein one side of the connection base in the axial direction is configured as a distal side towards the prosthetic heart valve, and the other side is configured as a proximal side away from the prosthetic heart valve. The holding arms are distributed around a periphery of the connection base, wherein the holding arms have positioning structures at the distal side thereof for engaging with an outflow side of the prosthetic heart valve.

In another aspect, the present invention provides a control handle joint, configured to be removably connected with a valve holder. The control handle joint includes an insertion portion configured to be removably inserted into the valve holder, and the insertion portion and the valve holder have an inserted condition and a detached condition. A limiting portion is connected with the insertion portion for limiting the valve holder in the inserted condition, and a connection portion between the limiting portion and the insertion portion is a deformable structure for releasing limitation on the valve holder. A control portion is connected with at least one of the limiting portion and the insertion portion.

In a further aspect, the present invention provides a system for delivering a prosthetic heart valve, which includes a prosthetic heart valve, and the valve holder as described above, wherein the prosthetic heart valve and the valve holder are positioned against each other and connected to each other by binding through a binding suture.

The valve holder of the present invention is optimized so that interferences from the valve holder to the retaining, positioning and releasing of the prosthetic heart valve can be avoided, and it also provides a structural base for other components coupled therewith, which improves the operation experience of the operator and the treatment effect.

Specific advantages will be further explained in connection with specific structures or steps in the detailed description.

BRIEF DESCRIPTION OF THE DRAWINGS

FIG. 1b is an enlarged view of a positioning structure of the valve holder shown in FIG. 1a;

FIG. 2a is another perspective view of the valve holder shown in FIG. 1a;

FIG. 2b is an enlarged view of a frame of the valve holder shown in FIG. 2a;

FIG. 3a is a side view of the valve holder shown in FIG. 2a;

FIG. 3b is a cross-sectional view of the valve holder shown in FIG. 2a;

FIG. 3c is a cross-sectional view of the valve holder shown in FIG. 3a;

FIG. 4 is a schematic view of a binding suture threading the valve holder shown in FIG. 2a;

FIG. 5 is an enlarged view of a suture routing groove of the valve holder shown in FIG. 1a;

FIG. 6b is another perspective view of the control handle joint shown in FIG. 6a;

FIG. 6c is a further perspective view of the control handle joint shown in FIG. 6a;

FIG. 7b is an enlarged cross-sectional view of a configuration at the position indicated by the letter A in FIG. 7a;

FIG. 8b is another perspective view of the valve holder and control handle joint shown in FIG. 8a;

FIG. 8c is a cross-sectional view of the valve holder and control handle joint shown in FIG. 8b, which shows the internal assembly relationship of the valve holder and the control handle joint;

FIG. 8d is a side view of the valve holder and control handle joint shown in FIG. 8c;

FIG. 9b is an exploded view of FIG. 9a;

FIG. 10b is a different schematic perspective view of FIG. 10a; and

DESCRIPTION OF THE EMBODIMENTS

The technical solutions according to the embodiments of the present disclosure will be described in combination with the drawings according to the embodiments of the present disclosure. The described embodiments represent some but not all the possible embodiments.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes any combinations of one or more of the listed options, as well as the combination of all of the listed options.

Figure 7A:
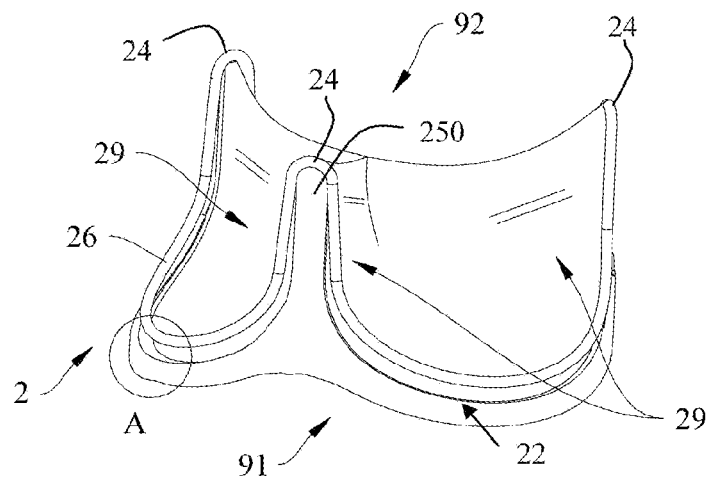
FIG. 7a is a schematic perspective view of an embodiment of a prosthetic heart valve.

Referring to FIGS. 1a to 5, the present invention describes an embodiment of a valve holder 1 for implanting a prosthetic heart valve 2 (as shown in FIG. 7a). The valve holder 1 includes a connection base 11 and holding arms 12 distributed around the periphery of the connection base 11. In this embodiment, a plurality of holding arms 12 are provided in spaced-apart manner along the circumferential direction of the connection base 11. The holding arms 12 function primarily to fix the relative positional relationship between the prosthetic heart valve 2 and the valve holder 1, so that the holding arms 12 can be distributed or spaced-apart to meet the mechanical requirements or the equivalent mechanical requirements for connecting the prosthetic heart valve 2 and the valve holder 1.

In this embodiment, the holding arms 12 and the connection base 11 are formed in one piece. In other embodiments, the holding arms and the connection base can be formed in separate pieces, in which case, the holding arms and the connection base should be connected to meet the strength requirement. In particular, the holding arms and the connection base can be connected through a fixed connection or a detachable connection. In the case of a fixed connection, the holding arms and the connection base can be separately produced and assembled by welding, bonding, heat fusing, riveting or other connection techniques which are not readily detachable. In the case of a detachable connection, the holding arms and the connection base can be separately produced and assembled by screwing, clamping, magnetic attraction or other connection techniques which are readily detachable and allow for a reconnection.

The connection base 11 in this embodiment has an axial direction, and in a working condition, one side of the connection base 11 in the axial direction is configured as a distal side 112 towards the prosthetic heart valve, and the other side is configured as a proximal side 113 away from the prosthetic heart valve. Having the valve holder 1 engaging with an outflow side 92 of the prosthetic heart valve 2 (as shown in FIG. 7a) can prevent the valve holder 1 from impacting the retaining, positioning and releasing of the prosthetic heart valve 2. In particular, the valve holder 1 is configured to be engaged with the outflow side 92 of the prosthetic heart valve 2 by positioning structures 13 provided at the distal side 112 of the holding arms 12 of the valve holder 1.

Figure 1A:
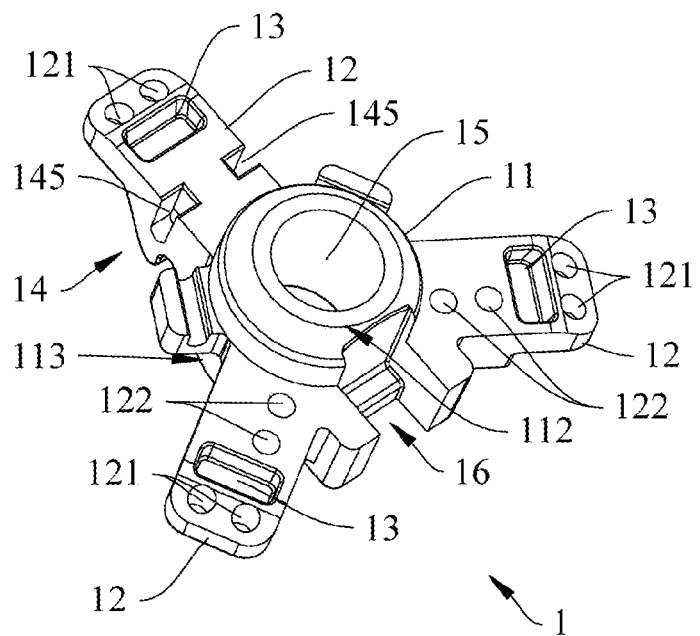
FIG. 1a is a schematic perspective view of an embodiment of a valve holder of the present invention.
Figure 1B:
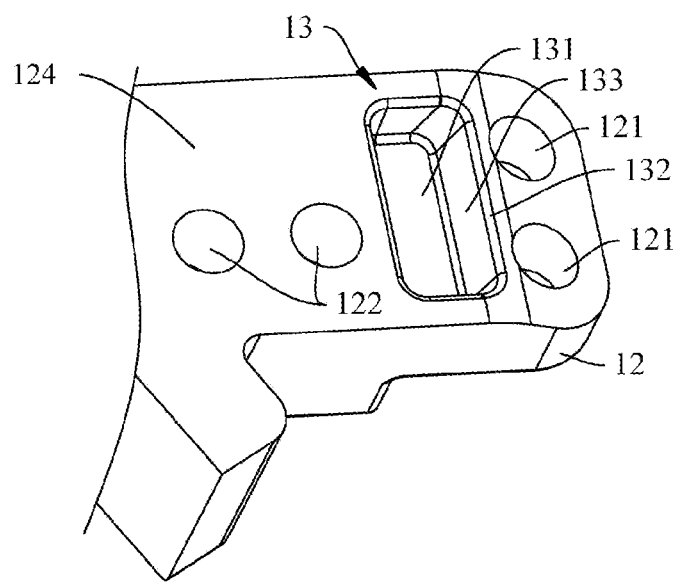
Figure 2A:
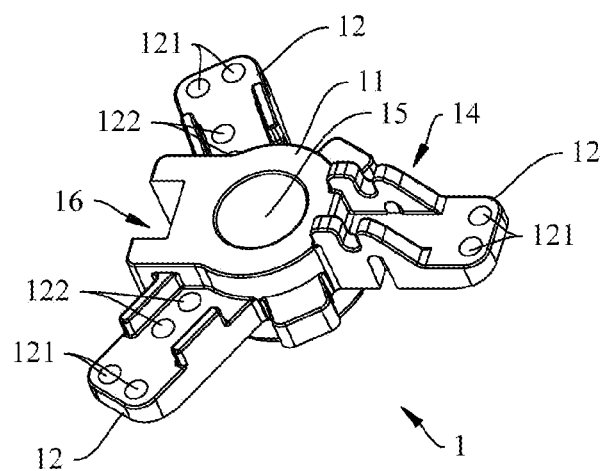
Figure 2B:
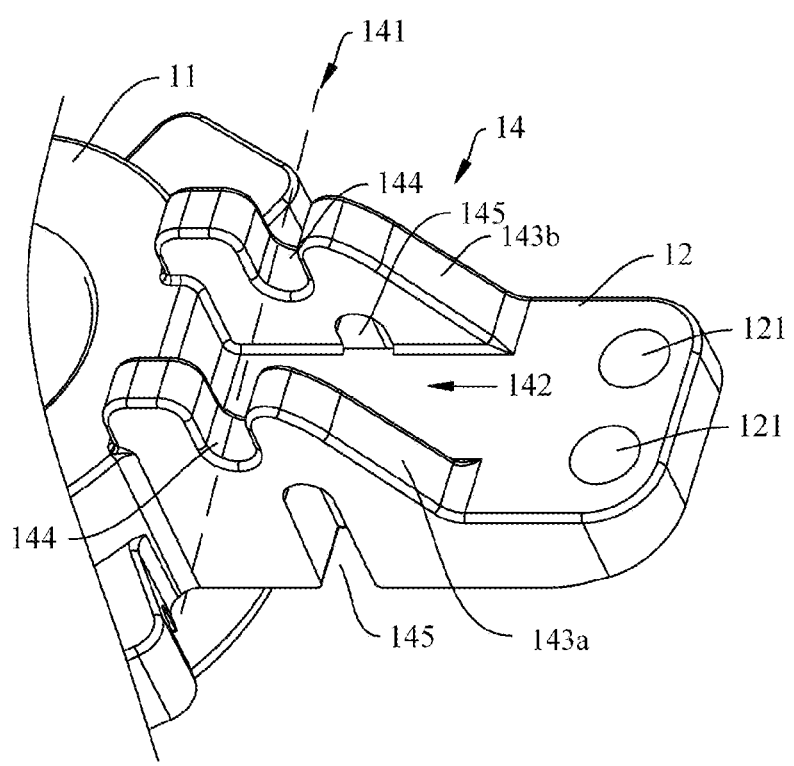

The positioning structure 13 can be configured as a structure which allows the valve holder 1 to be easily separated from the prosthetic heart valve 2, such as a clamping structure, a limiting structure, a bonding structure, a field-effect structure (e.g. a magnetic or electric field-effect structure) or the like. In the present embodiment, the positioning structure 13 is configured as an engaging groove 131, as shown in FIG. 1b.

The engaging grooves 131 can fix the relative positional relationship between the valve holder 1 and the prosthetic heart valve 2, and also enables the valve holder 1 to be easily separated from the prosthetic heart valve 2, thereby avoiding undesired damage to the prosthetic heart valve 2 caused by the valve holder 1 during the release of the prosthetic heart valve 2. It should be noted that, being contrary to the existing positioning structures, the engaging grooves 131 in this embodiment do not need to constrain the prosthetic heart valve 2 in all directions. In the present embodiment, the engaging groove 131 is opened in the axial direction of the valve holder 1, and the opening 132 of the engaging groove 131 is located at the distal side 112 and faces the prosthetic heart valve 2. It can be understood that the axial direction of the valve holder 1 is consistent with the axial direction of the prosthetic heart valve 2 when the valve holder 1 and the prosthetic heart valve 2 are assembled together. In other embodiments, a prevention structure can be provided at the opening 132 of the engaging groove 131 to prevent the prosthetic heart valve 2 from falling off the valve holder 1, and thereby improving the fixing effect. In the present embodiment, the opening 132 of the engaging groove 131 allows the prosthetic heart valve 2 to be removed from the valve holder 1 in the axial direction. The engaging groove 131 mainly functions to provide a radial constraint on the prosthetic heart valve 2. Particularly, the walls 133 of the engaging groove 131 provide a fastening force on the prosthetic heart valve 2 in a radially inward direction of the connection base 11.

The force from the walls 133 of the engaging groove 131 to the prosthetic heart valve 2 in the radially inward direction of the connection base 11 not only allows the positioning of the valve holder 1 and the prosthetic heart valve 2, but also enables the stent of the prosthetic heart valve 2 to be radially and inwardly deflected. Through the engagement with the engaging grooves 131, the prosthetic heart valve 2 is allowed to deform toward its own axis relative to its normal configuration, thereby enabling easier insertion of the heart valve 2 through the surgical opening and advancement to the annulus, thereby allowing the surgeon easier access to the sewing ring 21 for knot-tying purposes while still affording protection to the heart valve and the leaflets. This static deflection of the commissures of the prosthetic heart valve 2 radially inwardly when attached to the valve holder 1 is an important aspect of the present invention. As an example, the commissure tips of the prosthetic heart valve 2 can be deflected radially inwardly by 0.5-5 mm. Additionally, by providing a suitable material for the stent of the prosthetic heart valve 2, time-dependency can be reduced or even avoided.

The positioning effect of the engaging grooves 131 depends on the arrangement of the holding arms 12. In this embodiment, the plurality of holding arms 12 is arranged along the circumferential direction of the connection base 11 in a radial pattern. The holding arms 12 form a positioning plane relative to the connection base 11, and the engaging grooves 131 defined in the holding arms 12 can determine the spatial position of the prosthetic heart valve 2 relative to the positioning plane, which facilitates the retaining, positioning and releasing of the prosthetic heart valve 2. In the present embodiment, the holding arms 12 are evenly distributed on the periphery of the connection base 11 so that a regular and controllable positioning plane can be defined, which facilitates the assembly of the prosthetic heart valve 2 and the valve holder 1. Alternatively, in other embodiments, the holding arms can be unevenly distributed (i.e., spaced apart at different intervals) on the periphery of the connection base 11 to avoid corresponding anatomy.

The number of the holding arms 12 can range from 2 to 12. In a preferred embodiment, the number of the holding arms 12 ranges from 3 to 10, or 3 to 8, or 4 to 12, or 4 to 10.

Having an increased number of engaging grooves 131 can effectively improve the positioning effect of the valve holder 1 on the prosthetic heart valve 2. In the present embodiment, each of the arms 12 has an engaging groove 131, and the openings of all the engaging grooves 131 are oriented in the same direction. It should be noted that the "same direction" here is not only limited to the same geometric direction, but also includes the same orientation. For example, in some cases, all of the imaginary lines along the orientations of the openings 132 may point to the axis of the valve holder 1 and intersect at one point, where the openings 132 that are oriented regularly are also considered as being oriented in the "same direction", although the openings 132 can be geometrically different. In other embodiments, not all the holding arms have the engaging grooves 131, but only some of the holding arms (which function to position the prosthetic heart valve 2) have engaging grooves 131, thereby reducing the amount of machining needed.

Figure 3A:
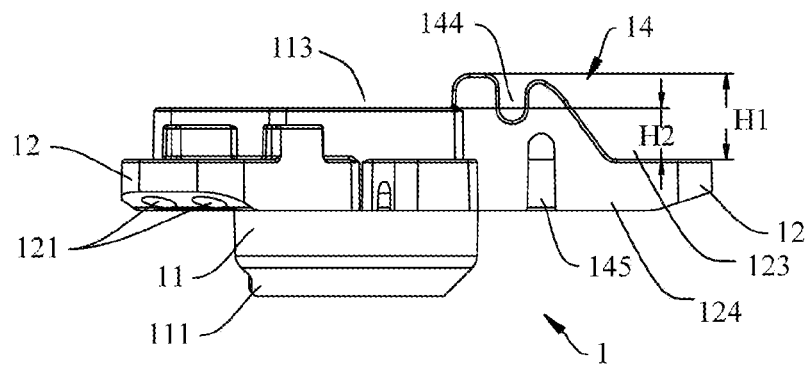
Figure 3B:
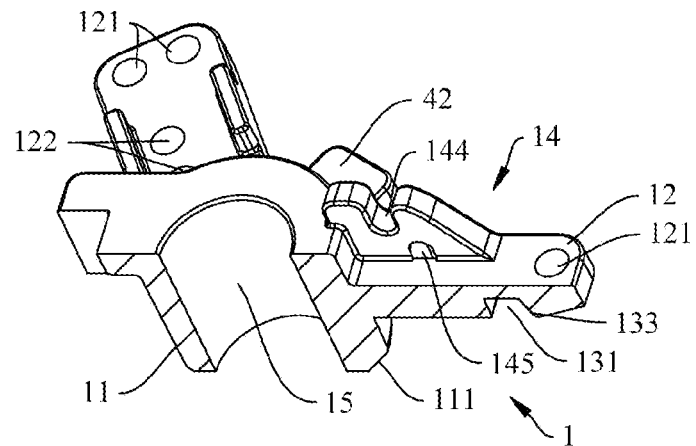
Figure 3C:
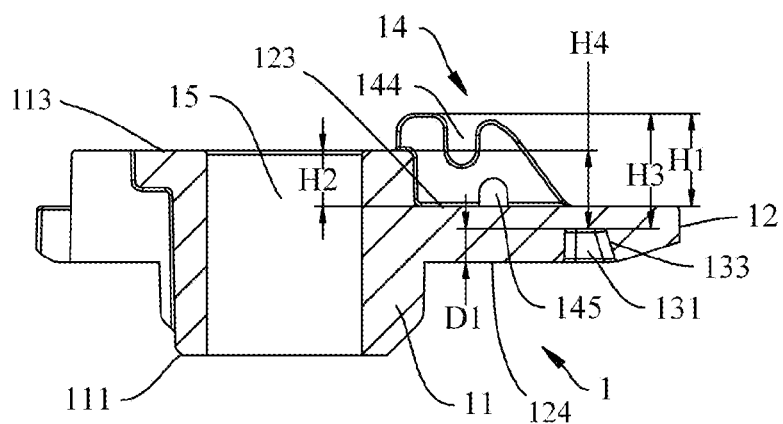

Referring to FIG. 3c, the depth D1 of the engaging groove 131 can range from 0.1 mm to 2.5. In a preferred embodiment, the depth D1 of the engaging groove 131 ranges from 0.6 mm to 2 mm, or 1 mm to 2.3 mm, or 0.8 mm to 2.3 mm.

Furthermore, the inventors have found that the existing valve holders that are available in the market can only be separated from the prosthetic heart valve by cutting binding sutures on the valve holder at three or more locations. Due to the anatomy, these locations for cutting the binding sutures are not all readily accessible, which can increase the operation time of the procedure. In addition, the cutting tool is typically sharp, which can cause damage to the anatomy of the patient, thereby increasing the operative risk to the patient.

In order to solve this problem, referring to FIGS. 1a to 5, one of the holding arms 12 of the valve holder 1 is preferably provided with a frame 14 for winding a binding suture 4 for binding the prosthetic heart valve 2. In the present embodiment, the frame 14 and the opening 132 of the engaging groove 131 are respectively located at two opposite sides of the holding arm 12. The frame 14 has a suture passing path 141 and a suture cutting opening 142 corresponding to the suture passing path 141. The suture passing path 141 allows sections of the binding suture 4 extending along the suture passing path 141 to be suspended.

The suture cutting opening 142 simplifies the suture cutting operation and reduces the operative risks. In particular, the suture cutting opening 142 can be defined separately, and a corresponding shielding structure can be provided to guide and shield the cutting tool. Furthermore, the binding suture 4 only has a single suture travel path that extends through the suture cutting opening 142, so that a single suture cutting operation at the suture cutting opening 142 can release the binding suture, thereby separating the valve holder 1 from the prosthetic heart valve 2, thereby effectively reducing the operation time. Depending on the anatomy, the operator can adjust the implantation direction of the prosthetic heart valve 2 to facilitate the operation at the suture cutting opening 142, which can effectively reduce the operative risk to the patient.

In the present embodiment, the frame 14 is fixed on one holding arm 12 and includes at least a pair of supporting seats 143a, 143b arranged opposite to each other. In particular, the two supporting seats 143a, 143b are respectively arranged at two opposite sides of the corresponding holding arm 12 along the circumferential direction of the connection base 11, and a gap between the supporting seats 143a, 143b defines the suture cutting opening 142. Each of the supporting seats 143a, 143b has a suture engaging groove 144 for threading the binding suture 4, and the suture passing path 141 is formed between the two suture engaging grooves 144 of the two supporting seats 143a, 143b. Furthermore, each of the supporting seats 143a, 143b defines a suture passing hole 145 for threading the binding suture 4. In the present embedment, the suture passing hole 145 is located at the bottom of the supporting seat 143a, 143b where the supporting seat 143a, 143b extends from the holding arm 12.

In order to enhance the constraint force from the holding arms 12 to the binding suture 4, at least one suture threading hole 121 is preferably defined in the holding arm 12 for threading the binding suture 4 for binding the prosthetic heart valve 2. Therefore, after the binding suture 4 is cut, all the fragments of the binding suture 4 are allowed to remain on the valve holder 1, thereby preventing any fragments of the binding suture 4 from remaining in the patient's body. More preferably, at least one of the holding arms 12 has a pair of suture knotting hole 122 for fixing the binding suture 4. The suture knotting hole 122 allows the fragments of the binding suture 4 to be easily retained on the valve holder 1. In the present embodiment, a pair of suture knotting holes 122 is defined in two of the holding arms 12.

Figure 4:
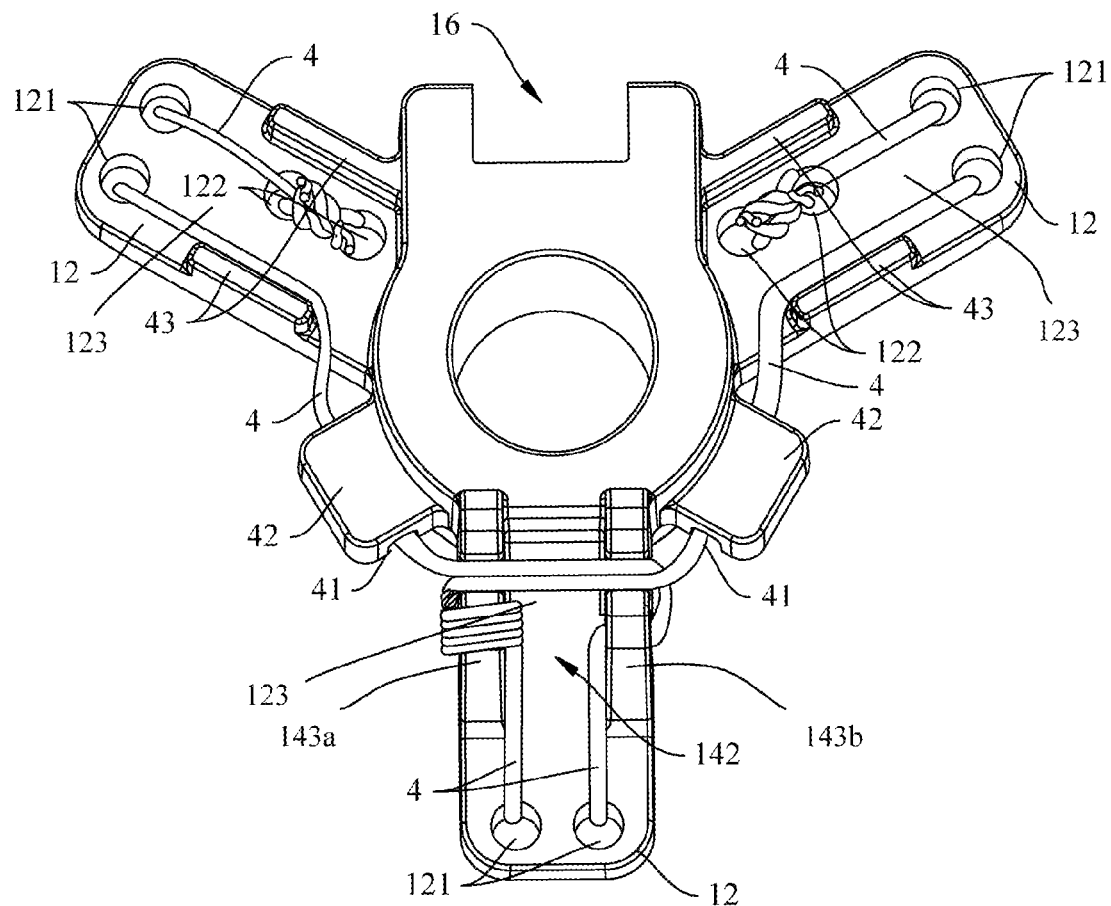
Figure 5:
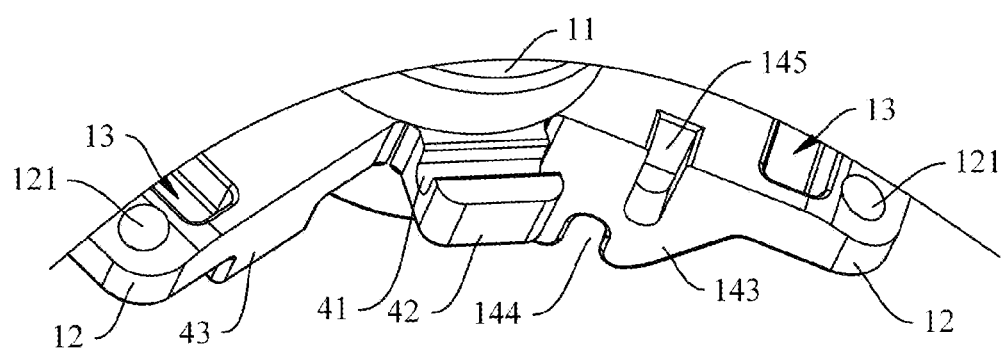

The arrangement of the binding suture 4 is an important point, and having the binding suture 4 being threaded in an inappropriate course may result in interferences or even a weakened constraint effect. Therefore, a suture routing groove 41 for threading the binding suture 4 is preferably defined between two adjacent holding arms 12, as shown in FIG. 4, and which faces or opens in the same direction as the engaging groove 131. In the present embodiment, the outer periphery of the connection base 11 is fixed with extension parts 42 that protrude radially and outwardly, with a suture routing groove 41 provided in each respective extension part 42.

The valve holder 1 can be further provided with structure on the holding arms 12 for defining the suture travel path. For example, in the present embodiment, at least one of the holding arms 12 is provided with suture blocking portions 43 for limiting the extension of the binding suture 4, as shown in FIG. 4.

In practice, the valve holder 1 is controlled by a control handle which will be described below. In the present embodiment, the connection base 11 defines an axially extending insertion hole 15 for engaging with the control handle joint 3 of the control handle, as shown in FIG. 3c. In particular, the connection base 11 has a generally cylindrical shape and the insertion hole 15 is formed as a through hole that extends axially through the connection base 11. In the present embodiment, the connection base 11 is further provided with an outer diameter tapering structure at the bottom side thereof. The outer diameter tapering structure can be formed by simultaneously tapering the inner side and outer side of the cylindrical shape, or can be formed as an outer wall chamfer 111 as shown in FIG. 3c. Furthermore, the connection base 11 is provided with a snapping portion 16 for engaging with the control handle joint 3, as shown in FIG. 1a. In the present embodiment, the snapping portion 16 is configured as a stepped structure.

The valve holder 1 in the present embodiment is optimized so that interferences from the valve holder 1 to the retaining, positioning and releasing of the prosthetic heart valve 2 can be avoided, and it also provides a structural base for other components coupled therewith, thereby improving the operation experience of the operator and the treatment effect.

Referring to FIGS. 3a to 3c, in the present embodiment, the holding arms 12 are located at the middle of the connection base 11 in the axial direction of the connection base 11. The holding arm 12 has opposite top and bottom sides 123, 124 in the axial direction of the connection base 11. The height H1 of the highest point of the frame 14 relative to the top side 123 of the holding arm 12 ranges from 1 mm to 4.5 mm. The height H2 of the proximal side 113 of the connection base 11 relative to the top side 123 of the holding arm 12 ranges from 0.5 mm to 2 mm. Relative to the top side 123 of the holding arm 12, the proximal side 113 of the connection base 11 is lower than the highest point of the frame 14. The height of the suture blocking portion 43 is 10% to 50% lower than the height of the connection base 11.

As shown in FIG. 3c, the height H3 from the bottom surface of the engaging groove 131 to the highest point of the frame 14 is only 3.1 mm. The height H4 between the bottom surface of the engaging groove 131 and the proximal side 113 of the connection base 11 is only 2.1 mm. Despite the dense anatomies within a patient, the valve holder 1 has a relatively flattened profile with the prosthetic heart valve 2, so it can be easily inserted into the body of the patient, and provides a better visibility for the operator during the implantation of the prosthetic heart valve 2.

The flattened, low-profile valve holder 1 has an improved visibility and therefore can easily pass through a narrow anatomical space. Furthermore, the valve holder 1 has an improved visibility and can be easily inserted into the body of the patient together with the prosthetic heart valve 2 so that the operation time can be reduced and the safety can be increased. Compared with the existing valve holders that have a relatively high, large profile, the flattened valve holder 1 in this embodiment avoids valve implantation difficulties and potential operational delays caused by an increased height.

Figure 11:
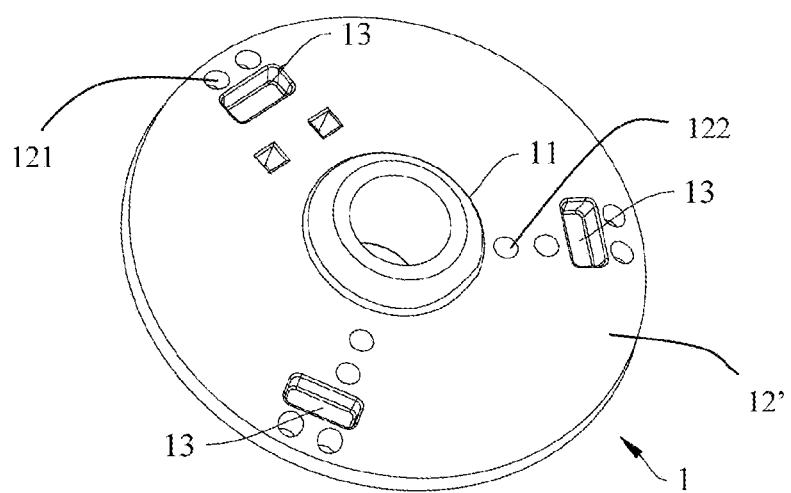
FIG. 11 is a schematic perspective view of another embodiment of a valve holder of the present invention.

In other embodiments, as shown in FIG. 11, the positioning structures 13 can be provided in a single disk, which can be considered as a single holding arm or disk 12' which is configured as a generally circular disk, instead of in the plurality of holding arms 12 provided in spaced-apart manner described above. The threading holes 121 described above can be defined in the disk 12' for threading the binding suture 4 for binding the prosthetic heart valve 2. Similarly, the suture knotting holes 122 can also be provided for fixing the binding suture 4.

Figure 7B:
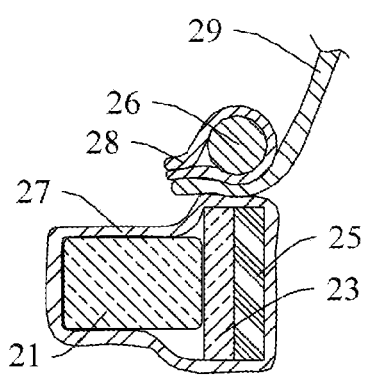

The valve holder 1 described above can be used to deliver the prosthetic heart valves 2 exemplarily shown in FIGS. 7a and 7b. It should be noted that the valve holder 1 disclosed herein is not limited to be used for the prosthetic heart valves 2 which will be described in detail below, but can be used for any other appropriate prosthetic heart valves.

The prosthetic heart valve 2 has an axial direction, with one side of the prosthetic heart valve 2 in the axial direction configured as an inflow side 91 for blood flow, and the other side configured as the outflow side 92 for blood flow. The prosthetic heart valve 2 includes a plurality of valve leaflets 29, a support structure 22, and a frame 26 for maintaining the configuration of leaflets 29. The holding arms 12 of the valve holder 1 are configured to be engaged with the proximal commissure tips 24 of the frame 26 of the prosthetic heart valve 2.

In this embodiment, the support structure 22 and frame 26 generally form an annular shape, and a blood flow channel is defined therethrough. In the support structure 22, the inflow side 91 and the outflow side 92 are opposite to each other in the axial direction of the annular shape. Specifically, the support structure 22 includes a first annular band 23, and a second annular band 25 having a plurality of extension bars 250 extending toward the outflow side 92 and spaced-apart from each other in the circumferential direction for supporting the proximal commissure tips 24 of the frame 26, where a commissure of adjacent leaflets 29 engages with the corresponding commissure tip 24. The plurality of leaflets 29 are connected to the support structure 22 for controlling blood flow.

The metal frame 26 does not undergo stress relaxation and permanent deformation over time when attached to the valve holder 1. In the present embodiment, the support structure 22 is fixed with a sewing ring 21 at the inflow side 91, and the annular bands as well as the sewing ring 21, as a whole, are covered by a first covering layer 27. The metal frame 26 is generally covered by a second covering layer 28.

Figure 7C:
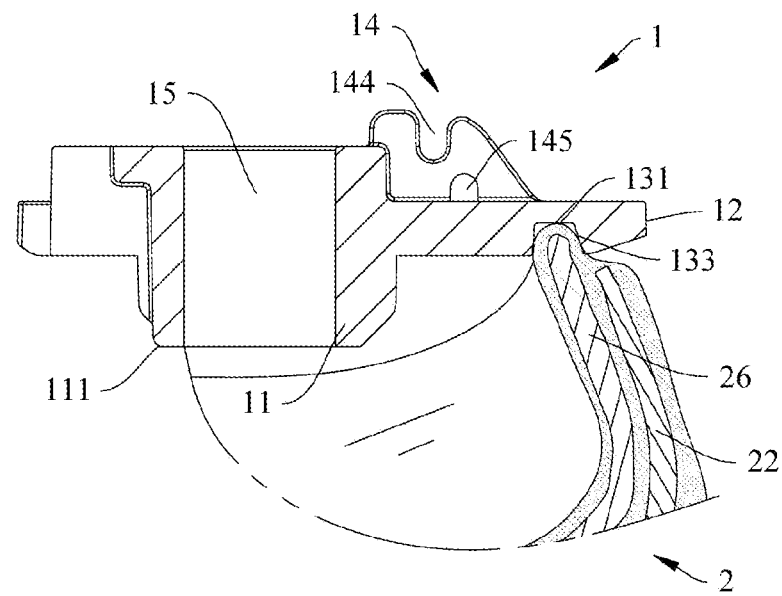
FIG. 7c is a partial view showing the valve holder engaging with the prosthetic heart valve.

When loading the prosthetic heart valve 2 onto the valve holder 1, the frame commissure tips 24 that are covered by the second covering layer 28 are inserted into the engaging grooves 131 of the holding arms 12 so that the prosthetic heart valve 2 is removably connected with the holding arms 12 through the engaging grooves 131, as shown in FIG. 7c. After the prosthetic heart valve 2 is loaded onto the valve holder 1, the valve holder 1 is positioned at the end of the prosthetic heart valve 2 away from the sewing ring 21 so that the valve holder 1 can be prevented from interfering with the sewing ring 21 during the retaining, positioning and releasing of the prosthetic heart valve 2. As mentioned above, the valve holder 1 pulls in the commissure tips 24 radially by about 0.5-5 mm to provide better access to the sewing ring 21.

With reference to FIGS. 1a to 5, 7a to 7c and 9b, the present invention further discloses a system that includes the prosthetic heart valve 2 and the valve holder 1 as described above, with the prosthetic heart valve 2 and the valve holder 1 positioned against each other and connected to each other by the binding suture 4.

All the sections of the binding suture 4 pass directly or indirectly through the suture cutting opening 142. At least one end of the binding suture 4 is fixed to the valve holder 1, particularly by at least one of the connection techniques consisting of connecting via a connector, adhering, and knotting.

The binding suture should be arranged to be stably connected with the valve holder 1 and to ensure that the fragments of the binding suture 4 after being cut can be retained on the valve holder 1. One winding method for the binding suture 4 will be described below with reference to FIG. 4. However, it should be noted that the binding suture 4 is not limited to be arranged using this winding method, but can be arranged using other appropriately modified winding methods.

Referring to FIG. 4, the binding suture 4 is first wound on the upper-left holding arm 12 shown in FIG. 4. Specifically, the binding suture 4 is first wound and fixed in the suture knotting holes 122 of the upper-left holding arm 12, and then inserted into one of the suture threading holes 121 along the top side 123 of the upper-left holding arm 12, and after that, it is connected to the corresponding portion of the prosthetic heart valve 2 by sewing, and then moved back to the top side 123 of the upper-left holding arm 12 through the other suture threading hole 121 of said the upper-left holding arm 12.

The binding suture 4 continues to extend along the top side 123 of the upper-left holding arm 12 along one of the suture blocking portions 43, through the lower-left suture routing groove 41, and into the frame 14. In particular, the binding suture 4 sequentially passes through the suture engaging grooves 144 of the two supporting seats 143a and 143b, and forms a suspended suture section along the suture passing path 141 corresponding to the suture cutting opening 142.

The binding suture 4 continues to pass through the suture passing hole 145 in the right supporting seat 143b shown in FIG. 4 and into the suture cutting opening 142, and then extends along the top side 123 of the corresponding holding arm 12 until it passes into one of the lower suture threading holes 121 shown in FIG. 4, and after that, it is connected to the corresponding portion of the prosthetic heart valve 2 by sewing, and then moved back to the top side 123 of the holding arm 12 through the other suture threading hole 121 of the holding arm 12.

The binding suture 4 continues to extend along the top side 123 of the corresponding holding arm 12 toward the left supporting seat 143a shown in FIG. 4, and passes back and forth through the suture passing hole 145 of the left supporting seat 143a shown in FIG. 4 to form a multi-turn configuration by binding and/or knotting. After that, the binding suture 4 passes through the suture engaging grooves 144 of the two supporting seats 143a, 143b again to form another suspended suture section along the suture passing path 141 corresponding to the suture cutting opening 142, and then passes through the lower-right suture routing groove 41 shown in FIG. 4 and extends to the upper-right holding arm 12 shown in FIG. 4.

The binding suture 4 extends along one of the suture blocking portions 43 on the top side 123 of the upper-right holding arm 12 shown in FIG. 4 until it passes into one of the upper-right suture threading holes 121 shown in FIG. 4. After that, it is connected to the corresponding portion of the prosthetic heart valve 2 by sewing, and then moves back to the top side 123 of the upper-right holding arm 12 shown in FIG. 4 through the other suture threading hole 121 of the holding arm 12, and finally, it is fastened in the suture knotting holes 122 of the holding arm, thereby forming the travel path of the binding suture 4.

Figure 6A:
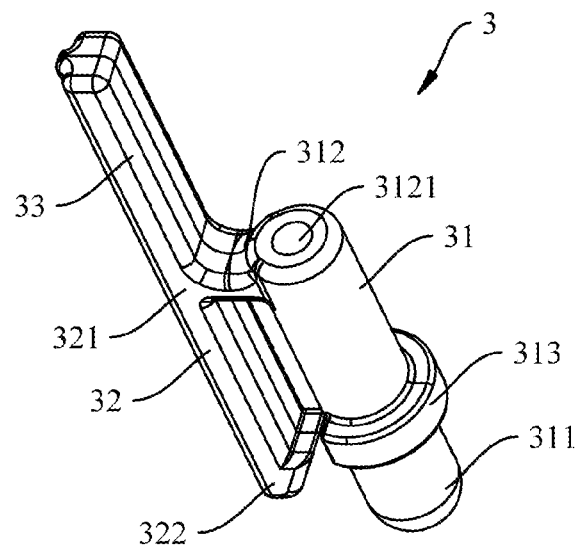
FIG. 6a is a schematic perspective view of an embodiment of a control handle joint of the present invention.
Figure 6B:
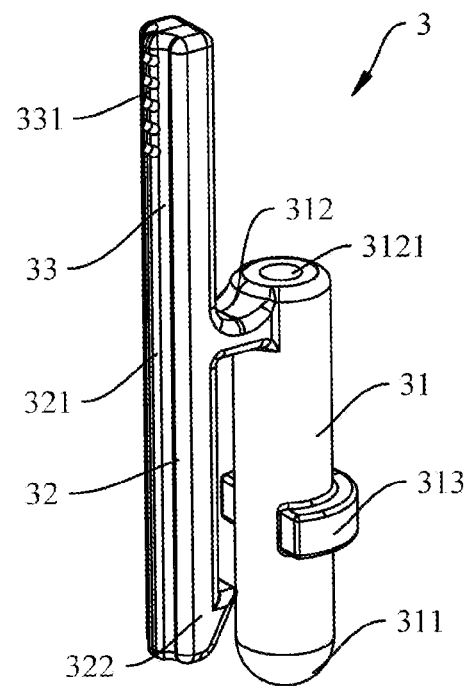
Figure 6C:
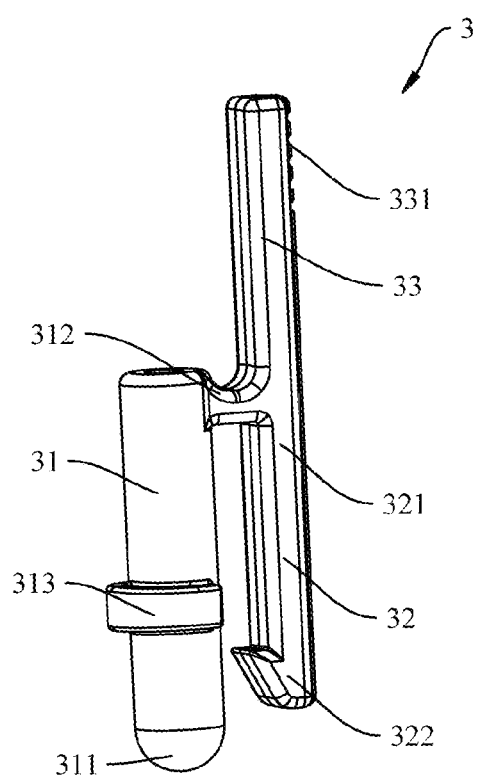

Referring to FIGS. 6a to 6c, the present invention further discloses an embodiment of a control handle joint 3 which is configured for being removably connected with the valve holder 1. The control handle joint 3 includes:

an insertion portion 31, which is configured to be removably inserted into the valve holder 1, and the insertion portion 31 and the valve holder 1 have an inserted condition and a detached condition;

a limiting portion 32, which is connected with the insertion portion 31 for limiting the valve holder 1 in the inserted condition, and the connection portion 312 of the limiting portion 32 and the insertion portion 31 is configured as a deformable structure for releasing the limitation on the valve holder 1; and a control portion 33, which is connected with at least one of the limiting portion 32 and the insertion portion 31, where the control portion 33 is provided with a friction surface 331 for increasing the friction force and improving the feel of the operator.

During the surgical procedure, the control handle joint 3 allows the prosthetic heart valve 2 to be seated properly and is configured to be connected to the valve holder 1 through the insertion portion 31, so that the operator can easily control the valve holder 1 and the prosthetic heart valve 2 mounted to the valve holder 1 through the control handle joint 3, and can switch the working condition of the control handle joint 3 and the valve holder 1 through the limiting portion 32.

The control handle joint 3 in this embodiment can be easily removed from the valve holder 1 after the prosthetic heart valve 2 is in place, with the valve holder 1 and the prosthetic heart valve 2 remaining assembled. However, the control handle joints that are available in the market are usually connected to a threaded interface of the valve holder and need to be curved during the surgical procedure, so that the control handle joint cannot be separated from the valve holder by rotation after the prosthetic heart valve is in place. Therefore, the presently-available control handle joints can only be removed by removing the valve holder from the prosthetic heart valve, particularly by cutting a plurality of binding sutures on the valve holder. After removal of the valve holder from the prosthetic heart valve, the prosthetic heart valve can no longer be protected by the valve holder in the subsequent suturing or other operations.

In this embodiment, the control handle joint 3 can be simply connected and removed, without affecting the connection between the valve holder 1 and the prosthetic heart valve 2, so that the valve holder 1 can protect the prosthetic heart valve 2. In particular, the valve holder 1 can provide a force on the prosthetic heart valve 2 in the radially inward direction of the connection base 11 to drive the portions of the prosthetic heart valve 2 to move toward each other, which avoids interference with the suturing operation from the prosthetic heart valve 2 and/or deformation of the prosthetic heart valve 2.

The deformable structure of the control handle joint 3 in the present embodiment shown in the drawings is made of an elastic material. Alternatively, in other embodiments, the deformable structure can be configured as a resettable hinge mechanism.

In this embodiment, the insertion portion 31 is rod-shaped, one end of which is an inserted end 311 for engaging with the valve holder 1, and the other end is adjacent to the connection portion 312 connected with the limiting portion 32. In the present embodiment, a fitting hole 3121 is defined in the insertion portion 31 and configured as a blind hole opened on the insertion portion 31, for mounting an auxiliary tool to control the control handle joint 3. For example, the auxiliary tool may be a rod inserted and extending along the axial direction of the insertion portion 31, for achieving relative movement between the insertion portion 31 and the limiting portion 32. This rod can be the malleable connection shaft 342 described below, which can be bonded or insert-molded inside the insertion portion 31.

Further, the inserted end 311 has a rounded structure. The insertion portion 31 is provided with a blocking portion 313 protruding outwardly, and in the inserted condition, the blocking portion 313 abuts against the valve holder 1 to limit the axial position of the control handle joint 3 relative to the valve holder 1. The blocking portion 313 extends along the circumferential periphery of the insertion portion 31.

Figure 8A:
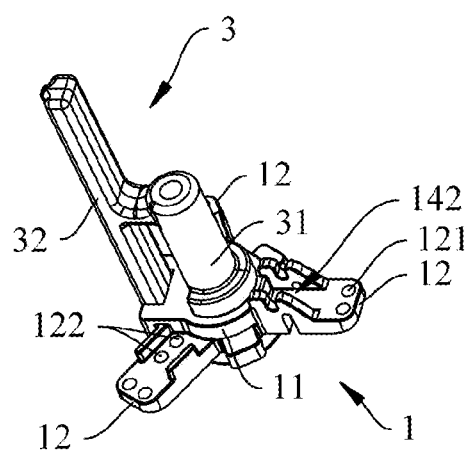
FIG. 8a is a schematic perspective view of the valve holder of FIG. 1 and the control handle joint of FIGS. 6a-6c being connected together.
Figure 8B:
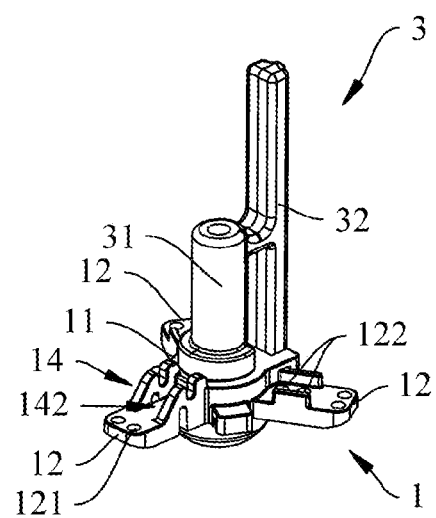

One end of the limiting portion 32 is a connection end 321 connected with the insertion portion 31, and the other end is a limiting end 322 for engaging with the valve holder 1. Further, the limiting end 322 is hook-shaped for engaging with the snapping portion 16 on the connection base 11, as best shown in FIGS. 8c and 8d.

The inserted end 311 extends beyond the limiting end 322 in the axial direction by about 2% to 30%. The control portion 33 is fixedly connected with the limiting portion 32. The control portion 33 and the limiting portion 32 are both rod-shaped and have the same extending direction. The limiting portion 32 and the insertion portion 31 are arranged substantially in parallel. Preferably, the insertion portion 31, the limiting portion 32 and the control portion 33 are formed in one piece.

FIGS. 1a to 8d illustrate the delivery assembly for a prosthetic heart valve 2, which includes the valve holder 1 and the control handle joint 3 as described above. The valve holder 1 is removably connected with the control handle joint 3.

Figure 9A:
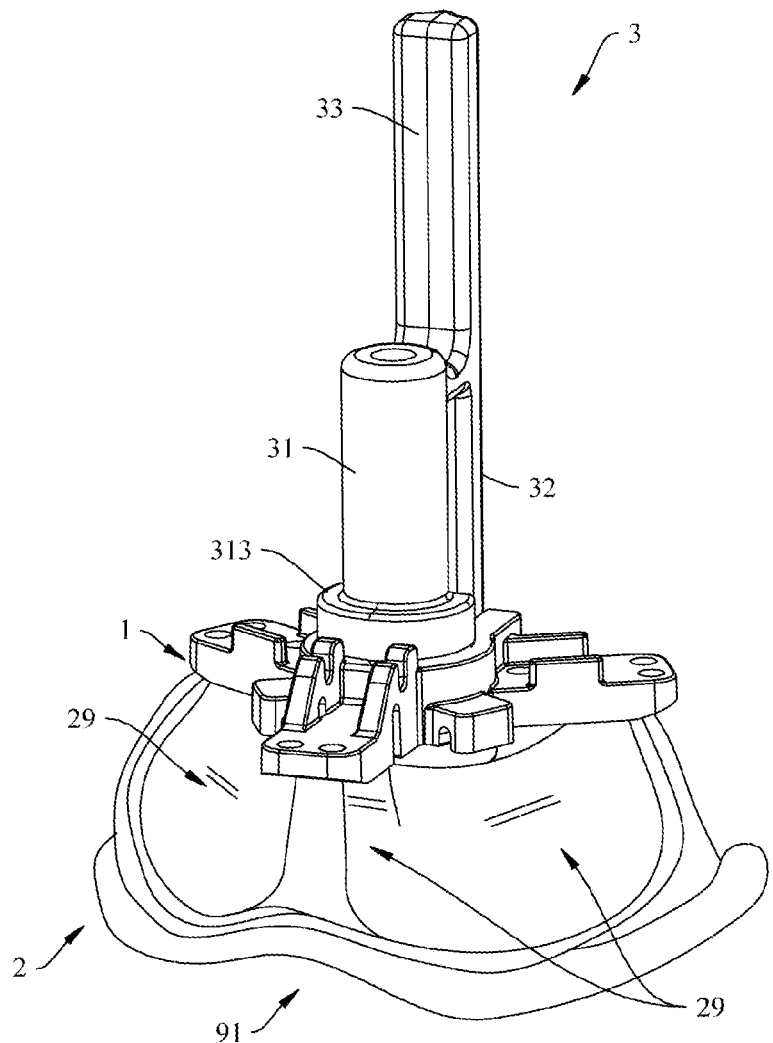
FIG. 9a is a schematic perspective view showing a prosthetic heart valve connected to the valve holder, and the valve holder connected to the control handle joint.
Figure 9B:
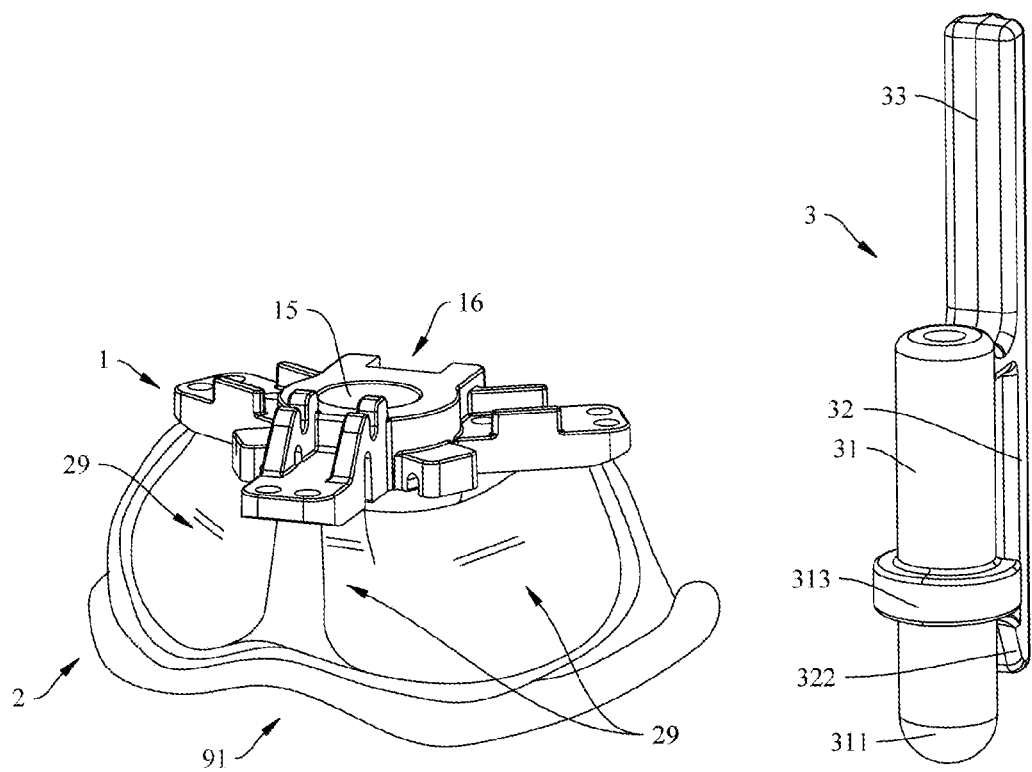

FIGS. 9a and 9b additionally illustrate the prosthetic heart valve 2 and the valve holder 1 positioned against each other and connected to each other by the binding suture 4, and the control handle joint 3 removably connected with the valve holder 1.

Figure 10A:
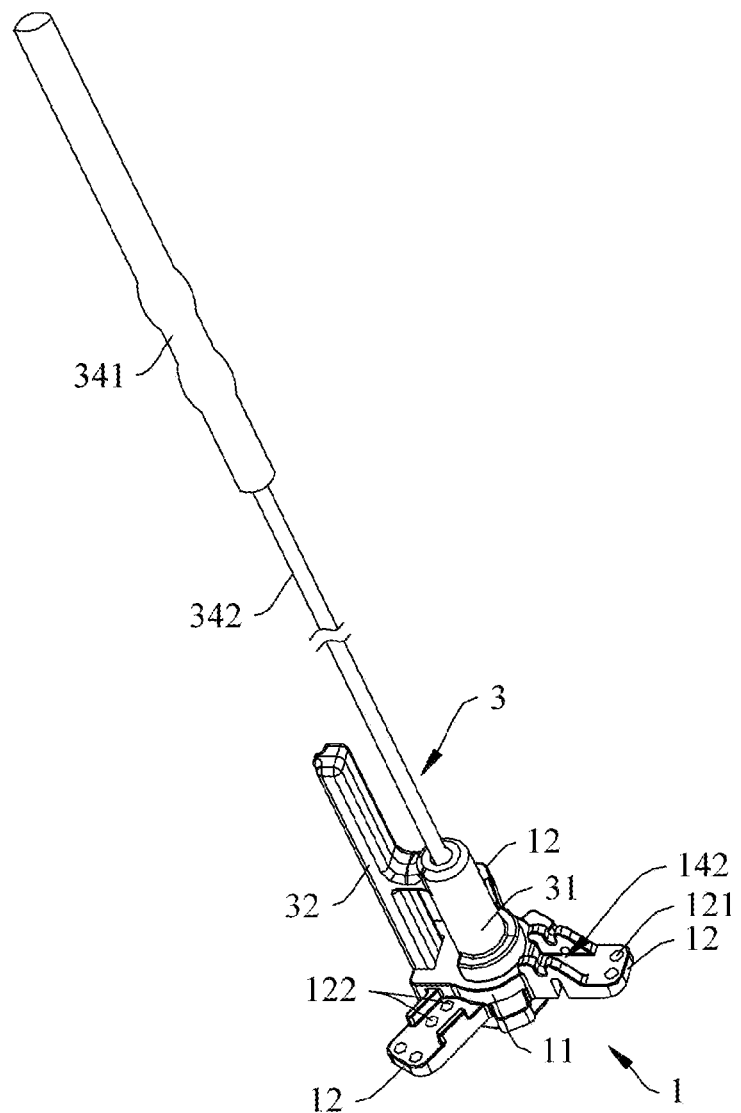
FIG. 10a is a schematic perspective view of an embodiment of a delivery device for a prosthetic heart valve of the present invention, which includes the control handle coupled to the valve holder.

FIG. 10a additionally shows the control handle, which includes a handle 341, a malleable connection shaft 342, and the control handle joint 3 described above, with one end of the connection shaft 342 connected with the handle 341, and the other end of the connection shaft 342 connected with the control handle joint 3. The connection shaft 342 can be made of metal or plastic or other materials having a certain rigidity. Preferably, the connection shaft 342 is bonded to the handle 341, and is inserted into the fitting hole 3121 provided on the control handle joint 3.

Finally, the control handle is connected with the valve holder 1 by inserting the inserted end 311 of the control handle joint 3 into the insertion hole 15 of the valve holder 1.

Figure 10B:
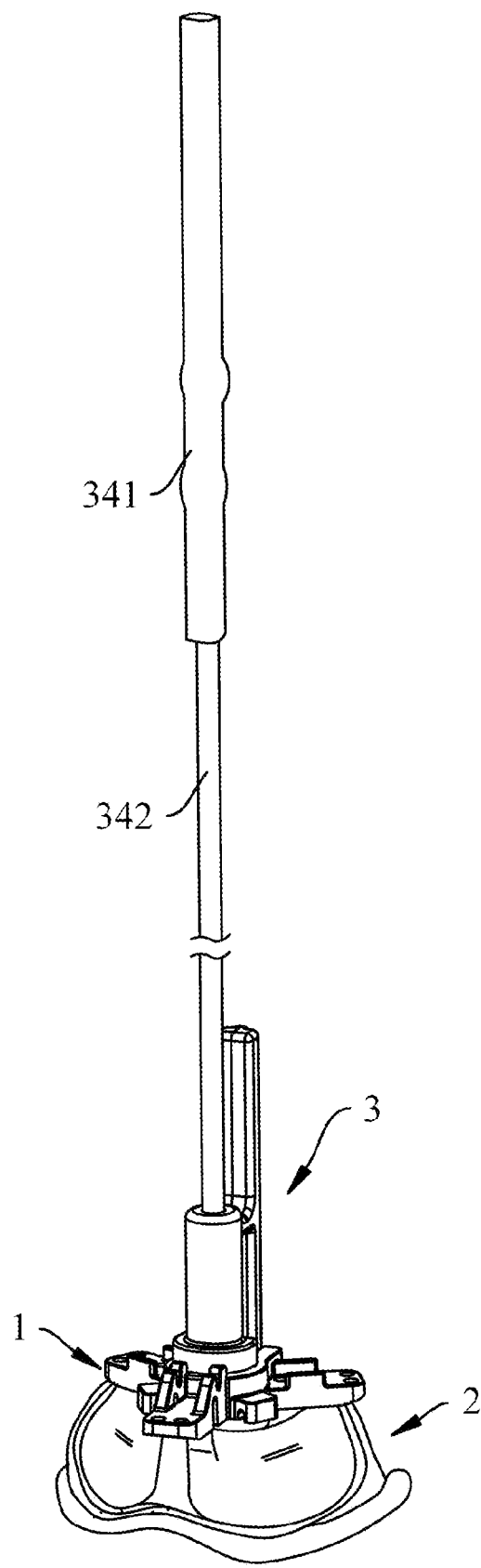

As shown in FIG. 10b, the operator can simply position the valve holder 1 and the prosthetic heart valve 2 through the handle 341.

The present invention can be implemented in the following manner.

First, the prosthetic heart valve 2 can be coupled to the valve holder 1 by abutting the outflow side 92 of the prosthetic heart valve 2 against the valve holder 1, and then binding the prosthetic heart valve 2 and the valve holder 1 through the binding suture 4 using the suturing technique described above. Optionally, the prosthetic heart valve 2 and the valve holder 1 can be provided together in a package in a bound state through the binding suture 4. Further, in the package, the valve holder 1 can be oriented towards the opening of the package for engaging with a preset component for the convenient removal of the valve holder 1 and the prosthetic heart valve 2. As an example, the control handle joint 3 can be configured as the preset component.

In the next step, the control handle joint 3 is made to engage the valve holder 1 by the techniques described above. Once the patient's native leaflets are removed and the annular sutures are placed, the sutures are sewn through the sewing ring 21 of the prosthetic heart valve 2.

Next, the combined prosthetic heart valve 2, the valve holder 1 and the control handle joint 3 are "parachuted" down the annular sutures, through an opened chest cavity of the patient to the patient's annulus where the prosthetic heart valve 2 is to be implanted.

Once the physician decides that the prosthetic heart valve 2 is in the correct position, the valve holder 1 and the control handle joint 3 are decoupled and separated from the prosthetic heart valve 2 to release the prosthetic heart valve 2.

The decoupling and separation of the prosthetic heart valve 2 is accomplished by cutting the binding suture 4 at the suture cutting opening 142 to release the binding suture 4, thereby decoupling and separating the valve holder 1, together with the binding suture 4, from the prosthetic heart valve 2.

Alternatively, the surgeon may elect to keep the valve holder 1 attached to the prosthetic heart valve 2 while tying the annular knots. The control handle joint 3 may be released from the valve holder 1 by depressing the control portion 33 and withdrawing the handle 341. Leaving the valve holder 1 attached to the prosthetic heart valve 2 during knot tying will allow better access to the sewing ring 21 adjacent to the commissures. After knot tying is complete, the holder can be removed by cutting the binding suture 4 at the suture cutting opening 142 and pulling the valve holder 1 from the prosthetic heart valve 2 using a surgical instrument. This alternative method takes full advantage of deflecting the commissures inward by allowing better access to the sewing ring 21.

The features described in the above various embodiments may be combined. In order to simplify the descriptions, not all possible combinations of the features in the above embodiments have been described. However, any combinations of the features should be within the scope of the invention as long as no conflict resides between these features. In the case where the features in different embodiments are shown in the same drawing, it may be considered that this drawing discloses a combination of the various embodiments involved.

The above embodiments are only several implementations of the present invention which are described specifically and in detail, without limitation to the scope claimed by the present invention. Those skilled in the art can make various modifications and variations to the embodiments without departing from the spirit and scope of the present invention, and these modifications and variations should fall into the scope claimed by the present invention.

What is claimed is:

1. A valve holder for delivering a prosthetic heart valve, comprising:
    a connection base, the connection base having an axial direction, wherein one side of the connection base in the axial direction is configured as a distal side towards the prosthetic heart valve, and the other side is configured as a proximal side away from the prosthetic heart valve;
    a plurality of holding arms distributed around a periphery of the connection base, wherein the plurality of holding arms has a positioning structure at the distal side thereof for engaging with an outflow side of the prosthetic heart valve; and
    a suture routing groove for threading a binding suture is defined between two adjacent holding arms.

2. The valve holder for delivering a prosthetic heart valve of claim 1, wherein the plurality of holding arms are provided at intervals in a circumferential direction of the connection base.

3. The valve holder for delivering a prosthetic heart valve of claim 1, wherein the positioning structure is an engaging groove.

4. The valve holder for delivering a prosthetic heart valve of claim 3, wherein each engaging groove has an opening, and the openings of all the engaging grooves are oriented in the same direction.

5. The valve holder for delivering a prosthetic heart valve of claim 3, wherein each engaging groove has a wall, and the walls of the engaging groove provide a fastening force on the prosthetic heart valve in a radially inward direction of the connection base.

6. The valve holder for delivering a prosthetic heart valve of claim 1, wherein the plurality of holding arms is provided with a frame for winding a binding suture for binding the prosthetic heart valve, the frame having a suture passing path and a suture cutting opening corresponding to the suture passing path, and the suture passing path causes a section of the binding suture extending along the suture passing path to be suspended.

7. The valve holder for delivering a prosthetic heart valve of claim 6, wherein each positioning structure is an engaging groove, each engaging groove has an opening, and openings of the engaging grooves and the frame are located at opposite sides of each of the plurality of holding arms along the axial direction of the connection base.

8. The valve holder for delivering a prosthetic heart valve of claim 6, wherein the frame comprises at least a pair of supporting seats arranged opposite to each other, and a gap between the supporting seats serves as the suture cutting opening.

9. The valve holder for delivering a prosthetic heart valve of claim 8, wherein each of the supporting seats defines a suture engaging groove for threading the binding suture, and the suture passing path is defined between the two suture engaging grooves.

10. The valve holder for delivering a prosthetic heart valve of claim 1, wherein each of the plurality of holding arms has at least one suture threading hole for threading a binding suture for binding the prosthetic heart valve.

11. The valve holder for delivering a prosthetic heart valve of claim 1, wherein the connection base has an axially extending insertion hole.

12. The valve holder for delivering a prosthetic heart valve of claim 11, wherein the connection base is provided with a snapping portion.

13. The valve holder for delivering a prosthetic heart valve of claim 1, wherein the plurality of holding arms is configured as a single disk, with the positioning structure provided at the distal side thereof for engaging with the outflow side of the prosthetic heart valve.

14. An assembly, comprising a valve holder for delivering a prosthetic heart valve and a control handle configured to be removably connected with the valve holder,
    wherein the valve holder comprises:
        a connection base, the connection base having an axial direction, wherein one side of the connection base in the axial direction is configured as a distal side towards the prosthetic heart valve, and the other side is configured as a proximal side away from the prosthetic heart valve; and
        at least one holding arm distributed around a periphery of the connection base, wherein the at least one holding arm has a positioning structure at the distal side thereof for engaging with an outflow side of the prosthetic heart valve;
    and wherein the control handle comprises:
    an insertion portion, configured to be removably inserted into the valve holder, and the insertion portion and the valve holder have an inserted condition and a detached condition,
    a limiting portion, connected with the insertion portion for limiting the valve holder in the inserted condition, and a connection portion between the limiting portion and the insertion portion is a deformable structure for releasing limitation on the valve holder, and
    a control portion, connected with at least one of the limiting portion and the insertion portion.

15. The assembly of claim 14, wherein the deformable structure is a resettable hinge mechanism or made of an elastic material.

16. The assembly of claim 14, wherein the insertion portion is provided with a blocking portion protruding outwardly and configured for abutting against and limiting the valve holder in the inserted condition.

17. The assembly of claim 14, wherein one end of the limiting portion is a connection end connected with the insertion portion, the other end is a limiting end for engaging with the valve holder, and the limiting end is hook-shaped.

18. A system, comprising
a prosthetic heart valve having an outflow side and a plurality of commissures, and
a valve holder, the valve holder comprising:
   a connection base, the connection base having an axial direction, wherein one side of the connection base in the axial direction is configured as a distal side towards the prosthetic heart valve, and the other side is configured as a proximal side away from the prosthetic heart valve,
and
   a plurality of holding arms distributed around a periphery of the connection base,
     wherein each of the plurality of holding arms has a positioning structure at the distal side thereof for engaging with the outflow side of the prosthetic heart valve and inwardly deflecting the plurality of commissures; and
     a suture routing groove for threading a binding suture is defined between two adjacent holding arms; and
   wherein the prosthetic heart valve and the valve holder are positioned against each other and connected to each other by binding through a binding suture.

19. The system of claim 18, wherein each of the plurality of holding arms is provided with a frame for winding a binding suture for binding the prosthetic heart valve, the frame has a suture passing path and a suture cutting opening corresponding to the suture passing path, and the suture passing path causes a section of the binding suture extending along the suture passing path to be suspended, and all sections of the binding suture pass directly or indirectly through the suture cutting opening.

20. The system of claim 19, wherein the prosthetic heart valve has an axial direction, one end of the prosthetic heart valve in the axial direction is provided with a sewing ring, and the other end thereof abuts against the valve holder.

\* \* \* \* \*